(12) United States Patent
Laghi

(10) Patent No.: US 6,702,859 B1
(45) Date of Patent: Mar. 9, 2004

(54) DYNAMIC PROSTHETIC FOOT WITH MULTIPLE LOAD POINTS AND ANTERIOR/POSTERIOR UPPER SECTIONS

(76) Inventor: Aldo A. Laghi, 14410 Eagle Point Dr., Clearwater, FL (US) 33762

( * ) Notice: Subject to any disclaimer, the term of this patent is extended or adjusted under 35 U.S.C. 154(b) by 51 days.

(21) Appl. No.: 10/064,839

(22) Filed: Aug. 22, 2002

(51) Int. Cl.[7] ................. A61F 2/66; A61F 2/68
(52) U.S. Cl. ................. 623/52; 623/55; 623/53
(58) Field of Search ................. 623/52–56, 47, 623/49

(56) References Cited

U.S. PATENT DOCUMENTS

| | | | | |
|---|---|---|---|---|
| 4,547,913 A | * | 10/1985 | Phillips | 623/27 |
| 4,645,509 A | * | 2/1987 | Poggi et al. | 623/55 |
| 4,822,363 A | * | 4/1989 | Phillips | 623/27 |
| 5,037,444 A | * | 8/1991 | Phillips | 623/55 |
| 5,116,384 A | * | 5/1992 | Wilson et al. | 623/49 |
| 5,219,365 A | * | 6/1993 | Sabolich | 623/55 |
| 5,258,039 A | * | 11/1993 | Goh et al. | 623/55 |
| 5,314,499 A | * | 5/1994 | Collier, Jr. | 623/47 |
| 5,387,246 A | * | 2/1995 | Phillips | 623/56 |
| 5,514,185 A | * | 5/1996 | Phillips | 623/52 |
| 5,571,210 A | * | 11/1996 | Lindh | 623/38 |
| 5,653,768 A | * | 8/1997 | Kania | 623/55 |
| 5,776,205 A | * | 7/1998 | Phillips | 623/55 |
| 5,800,570 A | * | 9/1998 | Collier | 623/55 |
| 5,899,944 A | * | 5/1999 | Phillips | 623/55 |
| 5,944,760 A | * | 8/1999 | Christensen | 623/55 |
| 6,007,582 A | * | 12/1999 | May | 623/55 |
| 6,053,946 A | * | 4/2000 | Wilkinson | 623/52 |
| 6,165,227 A | * | 12/2000 | Phillips | 623/53 |
| 6,197,068 B1 | * | 3/2001 | Christensen | 623/55 |
| 6,206,934 B1 | * | 3/2001 | Phillips | 623/53 |
| 6,254,643 B1 | * | 7/2001 | Phillips | 623/52 |
| 6,398,818 B1 | * | 6/2002 | Merlette et al. | 623/55 |
| 6,402,790 B1 | * | 6/2002 | Celebi | 623/38 |
| 6,511,514 B1 | * | 1/2003 | Wilson | 623/49 |
| 6,562,075 B2 | * | 5/2003 | Townsend et al. | 623/38 |
| 6,602,295 B1 | * | 8/2003 | Doddroe et al. | 623/55 |
| 2002/0087216 A1 | * | 7/2002 | Atkinson et al. | 623/38 |
| 2003/0045944 A1 | * | 3/2003 | Mosler et al. | 623/52 |

* cited by examiner

*Primary Examiner*—Corrine McDermott
*Assistant Examiner*—Alvin Stewart
(74) *Attorney, Agent, or Firm*—Ronald E. Smith; Smith & Hopen, P.A.

(57) ABSTRACT

A dynamic prosthetic foot having multiple load points and an anterior/posterior pair of upper sections includes a sole and an upper member. A heel end of the upper member has a gradual ninety degree bend formed in so that it is normal to the sole. An elongate longitudinally-extending slot divides the heel end of the upper member into a lateral, anterior pylon support and a medial, posterior pylon support and further divides the upper member into a lateral upper section and a medial upper section. The lateral, anterior pylon support is thicker than the medial, posterior pylon support and the lateral upper member section is thicker than the medial upper section so that forces applied to the lateral, anterior and medial, posterior pylons are transferred to a greater extent to the medial, posterior pylon. In a second embodiment, elongate pylons supplant the pylon supports.

20 Claims, 6 Drawing Sheets

DYNAMIC PROSTHETIC FOOT WITH MULTIPLE LOAD POINTS AND ANTERIOR/POSTERIOR UPPER SECTIONS

BACKGROUND OF INVENTION

1. Field of the Invention

This invention relates, generally, to the art of prosthetics. More particularly, it relates to improvements in prosthetic feet.

2. Description of the Prior Art

During normal ambulation, the first part of a foot to contact the ground is the free end of the heel. This initial contact between heel and ground is known as the "heel strike." The free end of the heel is soft and thus cushions the heel strike to at least some extent. The hard bottom of the heel is the next part of the foot to strike the ground; its hardness allows it to support the entire weight of the body. The foot continues to rotate in the well-known way until the toes "push off" at the end of a step.

Early prosthetic feet were quite rigid and provided little or no cushion to the impact on the ground at the moment of "heel strike" and little or no elastic response at "push off." The shock of impact was thus transmitted directly to the skeletal structure of the user, and the lack of elastic response forced an unnatural gait.

Perhaps the earliest prosthetic foot that provided an elastic response at heel strike and push off is disclosed in U.S. Pat. No. 4,547,913 to Phillips, assigned to Flex Foot, Inc. Multiple versions of that device have been developed. The original version is formed of a carbon fiber epoxy matrix consisting of a one-piece combination pylon upper and a one-piece sole. Mechanical fasteners interconnect the upper and the sole. In a second embodiment, the pylon is a round hollow tube and is connected by mechanical fasteners to a rectangular-shaped upper. A third version is like the first except that a standard Sach® foot adapter is employed to connect a standard prosthetic pylon. A fourth version is like the third but has a slightly different geometry. In a fifth version, an elastomeric glue connects the upper and the sole. In additional embodiments, leaf springs or hydraulic cylinders are incorporated into the prosthetic foot.

Although the developments in the art since the mid 1980s have significantly advanced the technology of prosthetic feet, the known prosthetic feet still provide little or no heel elasticity in a direction parallel to the ground. Instead, they provide elastic response in a vertical plane. Thus, although the impact at heel strike is reduced vis a vis the pre-1980's prosthetic feet, the reduced impact is transmitted vertically to the skeletal structure of the user, and the elastic response in a vertical plane causes a four to six millimeter bounce at heel strike. This vertical response causes an unnatural walk because a healthy human heel is soft at the back or free end where heel strike occurs and is hard on the bottom so that it can support the entire weight of the body. Thus, the normal gait of a human includes a rolling motion as the back of the heel strikes the ground; there is no vertical motion causing the heel to bounce upon ground impact. Accordingly, there remains a need for a prosthetic foot that provides substantial heel elasticity in a direction parallel to the ground.

A healthy human foot rolls on the lateral part of the foot during ambulation. The medial part of the foot provides a cushion and the force required at push off. Thus, there is a smooth transition from heel strike to push off, with no vertical dynamic response of the type that could cause the foot to bounce. Prosthetic feet of the type heretofore known, however, do not provide a smooth transition from heel strike to push off. This lack of a smooth transition produces what is known in the industry as a "flat spot." The presence of a flat spot between heel strike and push off produces an unnatural gait.

More particularly, the dynamic response is primarily vertical at the heel and the toe of a prosthetic foot. There is little or no component of the dynamic response in a horizontal plane as present in a healthy natural foot. The absence of dynamic response in a horizontal plane results in a step like motion going from an elastic vertical motion at heel strike to little or no support at mid-stance (the flat spot), and then again to an elastic vertical motion at push off.

There is a need, therefore, for a prosthetic foot having a dynamic response in a horizontal plane during heel strike, that provides a smooth transition between heel strike and push off to eliminate the flat spot, and that provides a dynamic response in a horizontal plane during push off.

The human foot provides a more rigid support laterally than medially. This design is advantageous because when an instability occurs, the weight of the person shifts from the rigid outer or lateral edge of the foot to the less rigid inner or medial edge. In this way, the prosthetic foot takes advantage of the presence of the natural foot, i.e., the lateral-to-medial motion experienced at the moment of an instability shifts additional support duties to the natural foot. One major drawback of the heretofore known prosthetic feet is the fact that such feet provide an exactly vertical response during ambulation with no component toward the medial section of the foot. Thus, if an instability in one foot urges the person to fall away from the natural foot, there is no shift of weight toward the medial part of the prosthetic foot as would occur in a natural foot, and the likelihood of a fall is substantially increased.

A prosthetic foot is therefore needed that has differentiated medial and lateral stiffness so that it can respond to instabilities in much the same way as a natural foot.

However, in view of the prior art considered as a whole at the time the present invention was made, it was not obvious to those of ordinary skill in the pertinent art how the identified needs could be fulfilled.

SUMMARY OF INVENTION

The long-standing but heretofore unfulfilled need for a dynamic prosthetic foot is now met by a new, useful, and nonobvious prosthetic foot having multiple load points and a pair of upper sections that are divided into an anterior upper section and a posterior upper section. The novel prosthetic foot includes a sole having a heel end and a toe end that are in substantially coplanar relation to one another and a pair of upper sections disposed normal to the sole. The upper sections are formed by longitudinally splitting an upper member having a heel end, a toe end, and a pair of flat, transversely spaced apart, pylon supports formed in its heel end. A first upper section is positioned toward the toe end of the foot in anterior relation to a second upper section that is positioned toward the heel end of the foot in posterior relation to the anterior section.

The heel end of each upper section has a gradual ninety degree bend formed therein so that the pylon supports are disposed substantially perpendicular to the sole. A transversely disposed parting line is formed where each pylon support separates from the sole.

Each pylon support is formed integrally with its associated upper section. The pylon supports include a lateral, anterior pylon support and a medial, posterior pylon support. An elongate slot is formed in the heel end of the upper member, substantially coincident with a longitudinal axis of the prosthetic foot. The slot extends from an uppermost end of the heel end of the upper member to a preselected point that is about two-thirds of the way from the heel of the sole to the toe of the sole.

Forces acting on the lateral pylon support are substantially confined to the lateral section of the upper member and forces acting on the medial pylon support are substantially confined to the medial section of the upper member.

Moreover, forces applied to the lateral, anterior pylon support are shifted in a posterior direction to the medial, posterior pylon support to mimic the operation of the fibula and tibia in a natural leg. The lateral, anterior pylon support performs the function of a fibula and the medial, posterior pylon support performs the function of a tibia. The lateral, anterior pylon support has a greater thickness than the medial, posterior pylon support and the medial member. The greater thickness imparts greater stiffness so that forces applied to the lateral, anterior pylon support and the medial, posterior pylon support are transferred more to the medial, posterior pylon support and medial section of the upper member than to the lateral, anterior pylon support and lateral section of the upper member, thereby mimicking the reaction of a natural foot to forces applied thereto.

The sole has a first convexity formed in the heel end that performs the function of the bottom of a natural heel. The sole has a concavity longitudinally spaced from the first convexity, said concavity performing the function of a natural arch. The sole has a second convexity longitudinally spaced from the concavity, said second convexity performing the function of the ball of a natural foot. The transverse parting line where the pylon supports separates from the sole are positioned in substantial juxtaposition with said concavity.

The elongate slot that divides the upper member into two upper sections has a heel end that is in open communication with the respective free ends of the lateral, anterior and medial, posterior pylon supports. The leading end of the slot extends to the point of inflection where the concavity formed in the sole meets the second convexity.

Pylon connectors are secured to the respective trailing sides of the pylon supports and elongate pylons are joined thereto.

In an alternative embodiment, the upper sections between the transverse parting line and the toe end of the sole are formed integrally with one another.

In a second embodiment of the invention, elongate pylons supplant the pylon supports and connectors.

An important object of the invention is to provide a prosthetic foot having a smooth transition from heel strike to push off.

Yet another object is to provide a prosthetic foot having differentiated medial and lateral stiffness so that an instability tends to shift weight from the lateral edge of the prosthetic foot to the medial edge thereof, just as in a natural foot.

Another important object is to provide a dynamic prosthetic foot having connections to pylons that mimic the actions of a natural fibula and tibia.

Yet another object is to provide multiple pylon supports (first embodiment) or pylons (second embodiment) exhibiting lower torsional stiffness when compared to a single tube-type pylon support or pylon, respectively.

Another object is to provide a prosthetic foot that flexes in the medial lateral planes without having any moving surfaces, i.e., parts that wear and make noise when two surfaces move relative to each other, such as in a bushing or in a hinge.

Another important object is to provide a prosthetic foot having an improved rollover motion.

These and other important objects, advantages, and features of the invention will become clear as this description proceeds.

The invention accordingly comprises the features of construction, combination of elements, and arrangement of parts that will be exemplified in the description set forth hereinafter and the scope of the invention will be indicated in the claims.

BRIEF DESCRIPTION OF DRAWINGS

For a fuller understanding of the nature and objects of the invention, reference should be made to the following detailed description, taken in connection with the accompanying drawings, in which.

DETAILED DESCRIPTION

Figure 1:
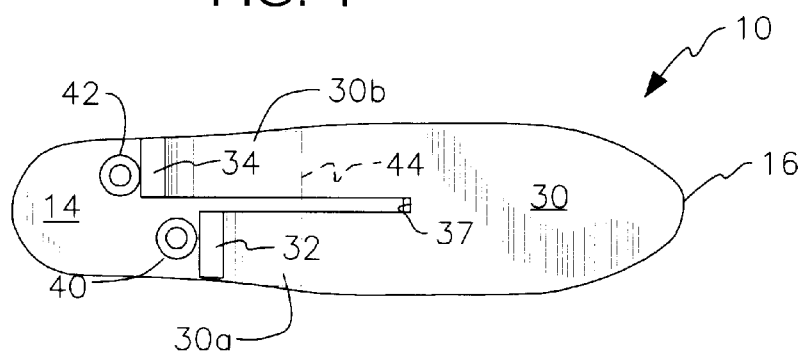
FIG. 1 is a top plan view of a prosthetic foot with multiple load points and a pair of upper sections including an anterior and a posterior upper section with truncate pylon supports and connectors.
Figure 2:
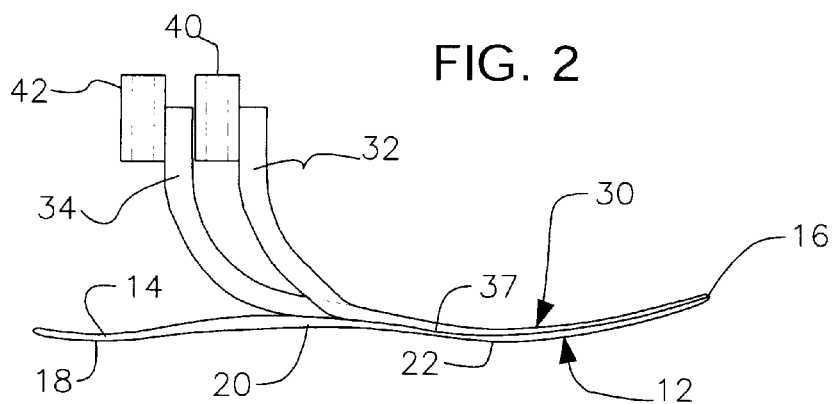
FIG. 2 is a side elevational view thereof.
Figure 3:
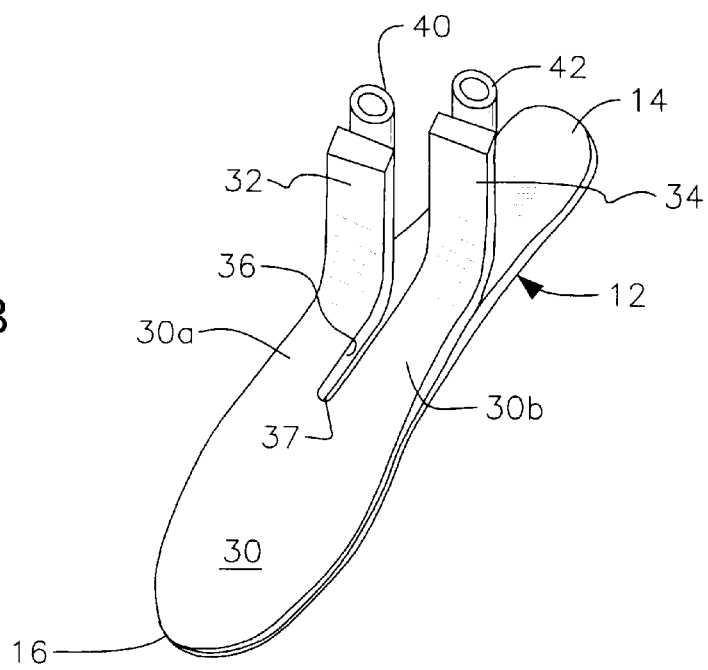
FIG. 3 is a perspective view thereof.

Referring to FIGS. 1–3, it will there be seen that the reference numeral 10 denotes an illustrative embodiment of the novel dynamic prosthetic foot having multiple load points and a pair of upper sections that includes a lateral, anterior pylon support and a medial, posterior pylon support.

Prosthetic foot 10 includes a sole 12 having a heel end 14 and a toe end 16 that are in substantially coplanar relation to one another. Relative to the ground, as best understood in connection with FIG. 2, sole 12 includes convexity 18 that performs the function of the bottom of a natural heel, concavity 20 that performs the function of a natural arch, and second convexity 22 that performs the function of the ball of a natural foot.

Upper member 30 includes a pair of flat, transversely spaced apart pylon supports 32, 34 that are separated from one another by elongate slot 36. Lateral, anterior pylon support 32 has a greater thickness than medial, posterior pylon support 34 as indicated in FIGS. 1 and 3. A gradual ninety degree bend formed in substantially horizontal upper member 30 that begins substantially at transverse parting line 44 forms said substantially vertical pylon supports 32, 34.

Elongate slot 36 has a first end in open communication with the respective free ends of pylon supports 32, 34, as perhaps best depicted in FIG. 3. The second end of slot 36 terminates about two-thirds of the way from heel to toe of foot 10. More particularly, elongate slot 36 terminates about where concavity 20 meets second convexity 22, as perhaps best understood in connection with FIG. 2. This point is denoted 37 in the drawings and may be understood as a point of inflection where the negative slope at the toe end of concavity 20 meets the positive slope at the heel end of second convexity 22. Although said concavity and convexity are formed in sole 12 and not in upper member 30, the overlying relation of upper member 30 to sole 12 enables the location of a reference point in sole 12 with respect to upper member 30.

The length of elongate slot 36 is sufficient to substantially divide upper member 30 into upper sections 30a and 30b. Each of said sections thus responds to forces appearing at heel 14 of foot 10 in substantially independent response. Moreover, since slot 36 extends to inflection point 37, said upper sections 30a and 30b also respond substantially independently to forces appearing about mid-length of foot 10, i.e., those forces appearing about mid-gait of a stride.

Pylon connectors 40, 42 are secured to the trailing ends of pylon supports 32, 34, respectively. Pylon connectors 40, 42 are adapted to engage the respective lower ends of elongate pylons, not shown, that interconnect prosthetic foot 10 and a prosthetic socket that receives a residual limb. The greater thickness and thus greater stiffness of lateral, anterior pylon support 32 ensures that instabilities appearing on foot 10 will be shifted in a medial direction, just like a natural foot. Slot 36 enables lateral, anterior pylon support 32 to respond to instabilities substantially independently of medial, posterior pylon support 34, and vice versa . Thus, forces acting upon a lateral section of said upper member are substantially attenuated when transmitted to the medial section of said upper sections and forces acting upon a medial section of said upper member are substantially attenuated when transmitted to the lateral section of said upper member.

Moreover, lateral anterior pylon support 32 simulates a fibula in a natural leg and medial, posterior pylon support 34 simulates a tibia in a natural leg.

Pylon supports 32, 34 are curved as depicted so that they gradually join upper member 30 at transverse parting line 44 that is about mid-length of arch concavity 20. Upper members 30a and 30b overlie and abut sole 12 from line 44 to toe end 46 thereof. The thickness of upper members 30a and 30b gradually decrease as depicted as they extend from said point 44 to said toe end. The combined thickness of sole 12 and upper member 30 at said toe end is substantially the same as the thickness of the heel end 14 of sole 12. The elastic response of said heel and toe ends of said sole 12 are thus controlled by the thickness of the sole and upper member so as to provide differentiating elastic response for patients of differing weights and/or of different activity levels.

Figure 4:
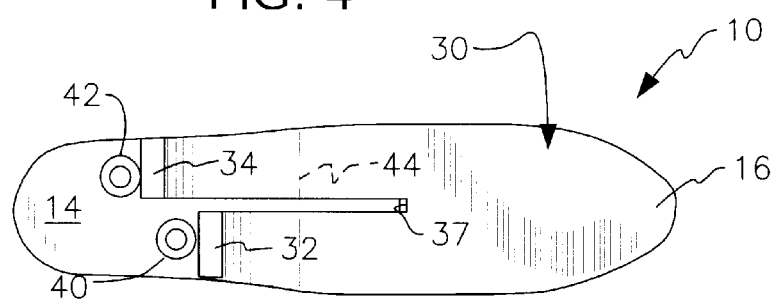
FIG. 4 is a top plan view of a second embodiment of said FIG. 1 prosthetic foot.
Figure 5:
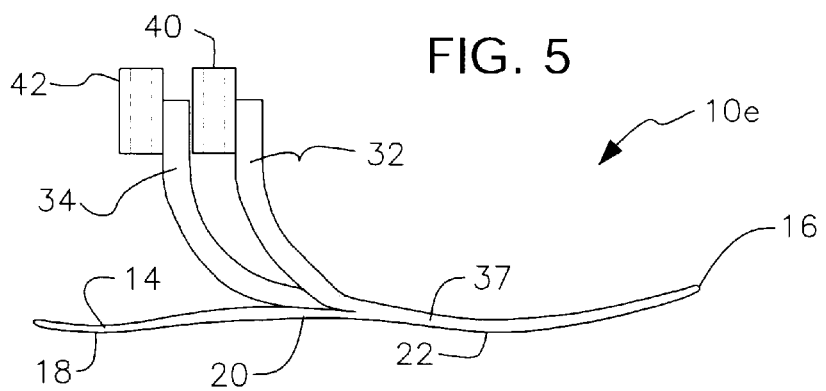
FIG. 5 is a side elevational view of said FIG. 4 second embodiment.
Figure 6:
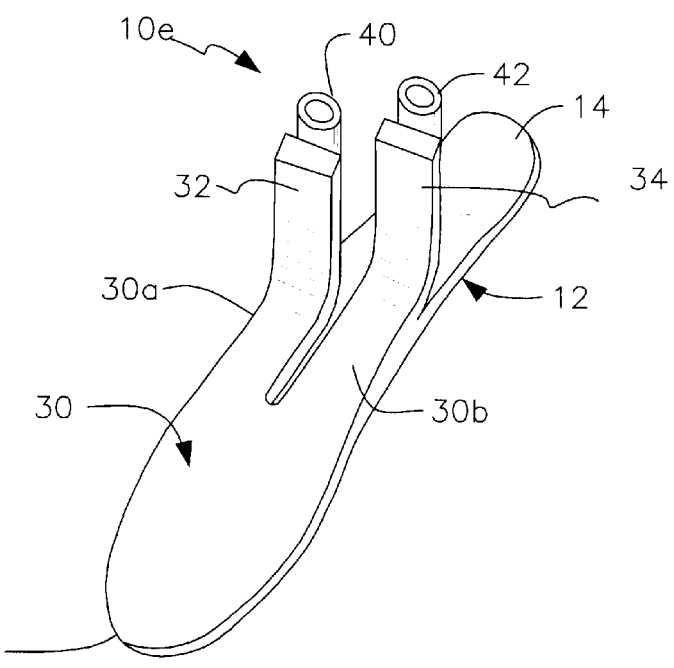
FIG. 6 is a perspective view of said FIG. 4 second embodiment.

The alternative embodiment of FIGS. 4–6 is like the embodiment of FIGS. 1–3 in all respects except that sole 12 and upper member 30, divided into upper sections 30a, 30b as aforesaid, are of unitary construction in the latter embodiment in the region between parting line 44 and the toe end of the prosthetic foot.

Figure 7:
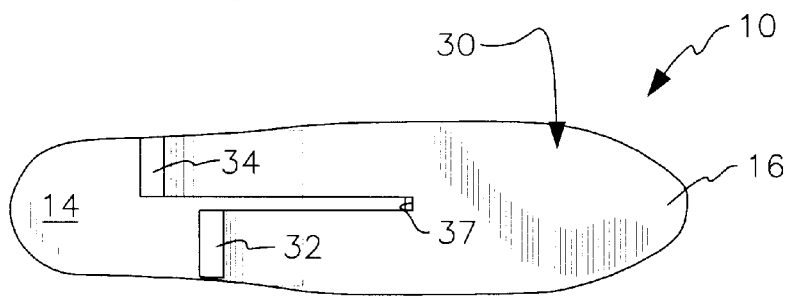
FIG. 7 is a top plan view of a prosthetic foot with multiple load points and multiple upper sections and having elongate pylons.
Figure 8:
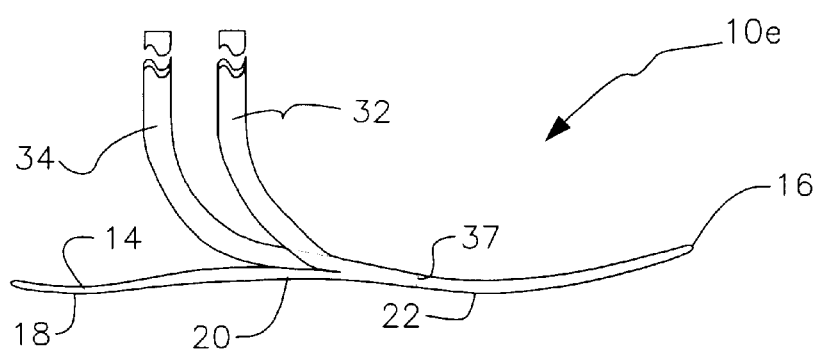
FIG. 8 is a side elevational view thereof.
Figure 9:
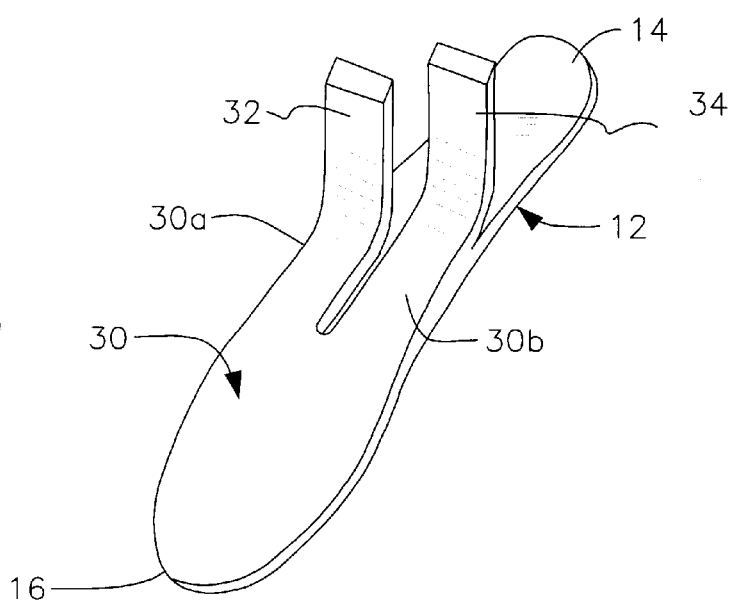
FIG. 9 is a perspective view thereof.

The embodiment of FIGS. 7–9 differs from the embodiment of FIGS. 1–3 in that pylon supports 32, 34 are supplanted by elongate pylons 32a, 34a having a length of about twenty inches (20"). This eliminates the need for pylon connectors 40, 42. Pylons 32a, 34a are cut to size by the prosthetist when the prosthetic foot is fitted onto the patient.

Figure 10:
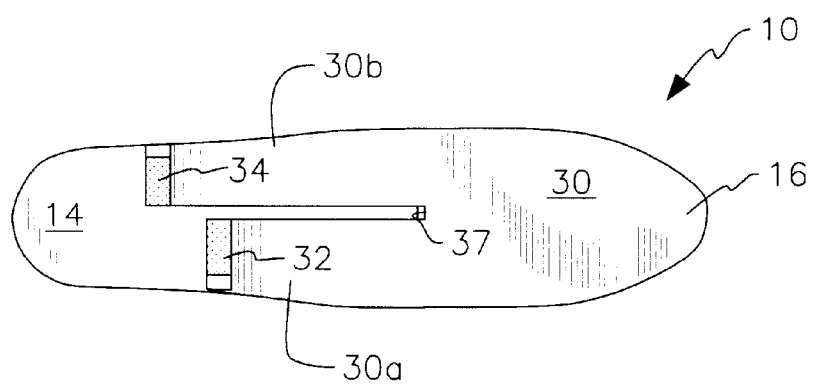
FIG. 10 is a top plan view of a second embodiment of the prosthetic foot of FIG. 7.
Figure 11:
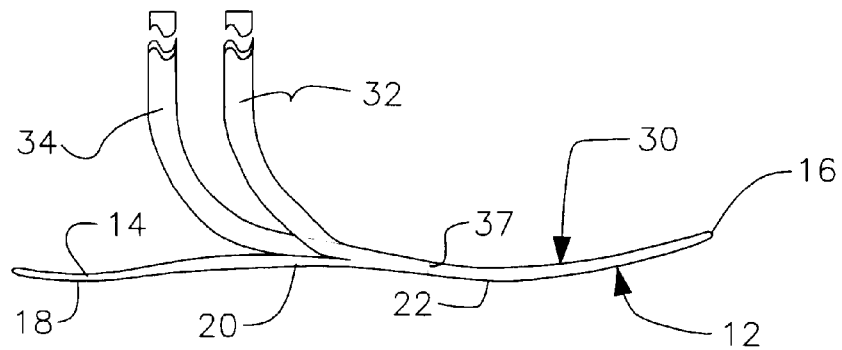
FIG. 11 is a side elevational view of said FIG. 10 second embodiment.
Figure 12:
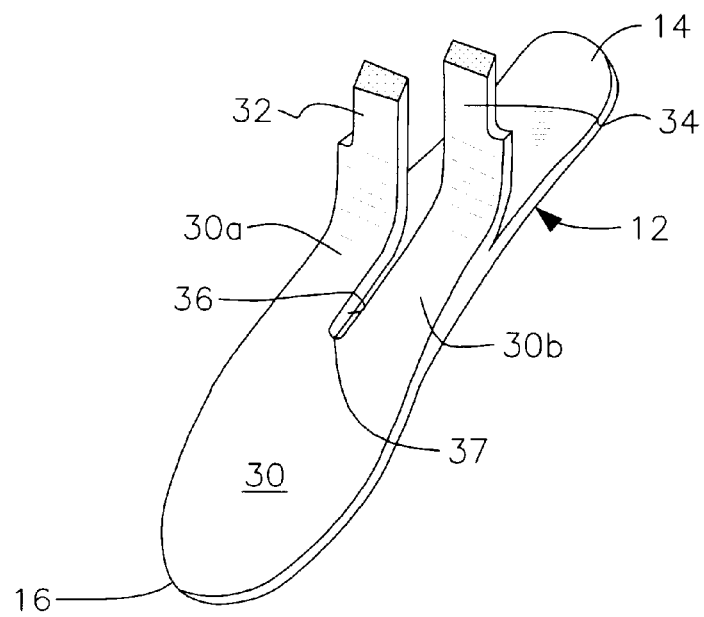
FIG. 12 is a perspective view of said FIG. 10 second embodiment.

The embodiment of FIGS. 10–12 similarly differs from the embodiment of FIGS. 4–6 in that pylon supports 32, 34 are replaced by elongate pylons 32a, 34a having a length of about twenty inches (20"). This eliminates the need for pylon connectors 40, 42. Moreover, sole 12 and upper member 30, divided into upper sections 30a, 30b in FIGS. 7–9, are of unitary construction in the embodiment of FIGS. 10–12 in the region between transverse parting line 44 and toe end 16 of prosthetic foot 10.

Figure 13:
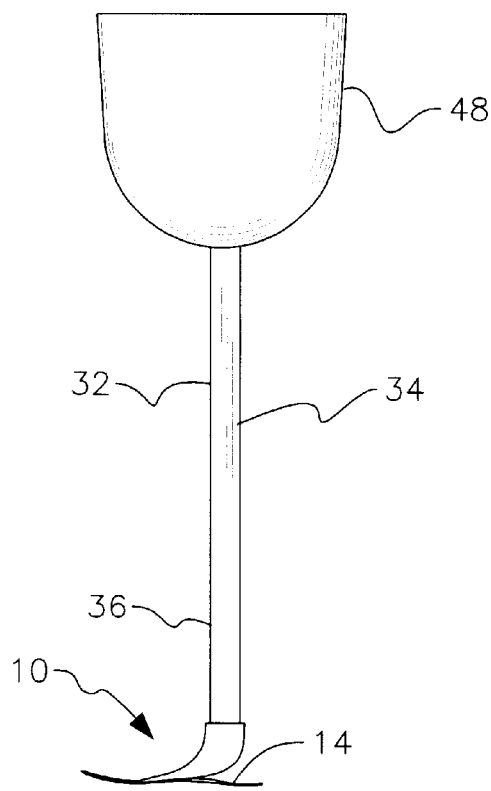
FIG. 13 is a perspective view of the elongate pylons embodiment when attached to a socket.

FIG. 13 depicts the novel structure when equipped with elongate pylons 32a, 34a.

After pylons 32a, 34a have been cut to a desired length, the prosthetist has several options by which the pylons may be connected to prosthetic socket 48. Pylons 32a, 34a may be laminated into prosthetic socket 48 as illustrated in said FIG. 13. This forms a permanent connection between pylons 32a, 34a and socket 48.

Figure 14:
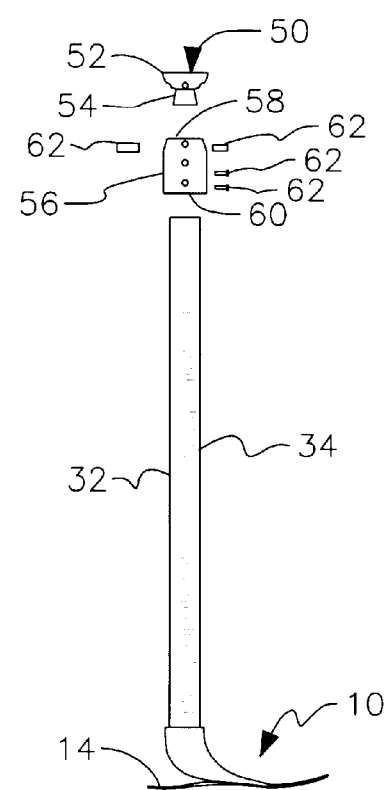
FIG. 14 is a perspective view of the elongate pylons embodiment and further depicting connector means, in exploded form, for connecting said elongate pylons to a socket.

A second option includes the use of a commercially available pyramid connector 50 as depicted in FIG. 14. Such pyramid connectors have been in use for fifty or so years. Pyramid connector 50 includes upper part 52 and lower part 54 that depends from the upper part. Upper part 52 is attached to the lowermost or distal end of socket 48. A hollow pyramid-receiving connector 56 has an open upper end 58 that receives lower part 54 of pyramid connector 50 and an open lower end 60 that receives the respective uppermost ends of pylons 32a, 34a. Lower end 54 of pyramid connector 50 and the respective upper ends of pylons 32a, 34a are captured in said hollow pyramid-receiving connector 56 by a plurality of set screws, collectively denoted 62.

Pyramid connector 52 and pyramid-receiving connector 56 are employed to enable adjustment of the angle of pylons 32a, 34a so that prosthetic foot 10 falls in the correct medial/lateral and anterior/posterior planes, as perhaps best understood by making reference to FIG. 14.

A third option available to the prosthetist after cutting the pylons to their correct length is to laminate the pylons to an unillustrated component and to attach that component to the socket.

Figure 15A:
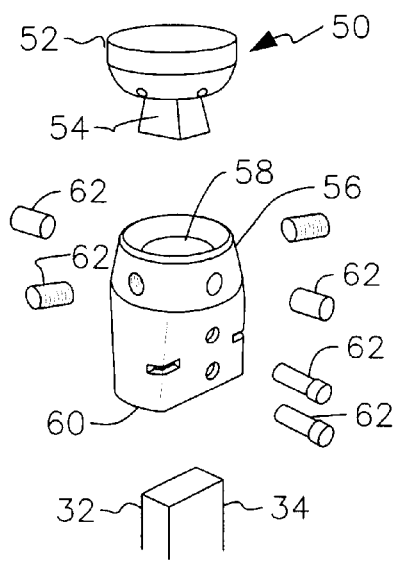
FIG. 15A is an exploded first perspective view of said connector means.
Figure 15B:
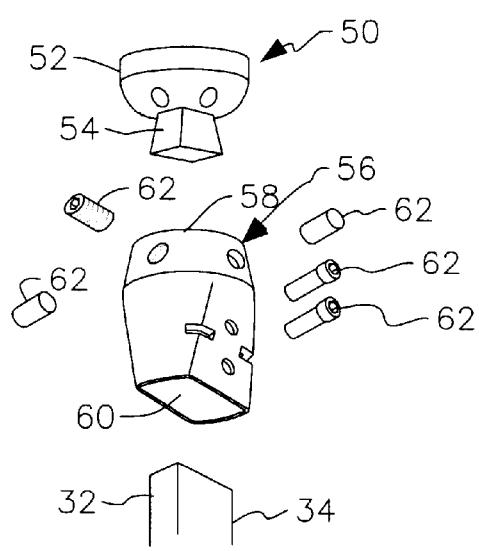
FIG. 15B is an exploded second perspective view of said connector means.
Figure 15C:
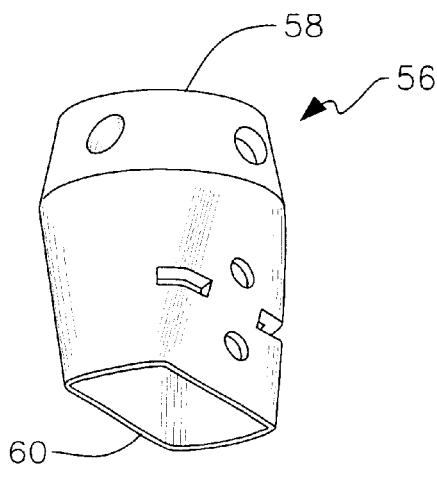
FIG. 15C is a first perspective view of a pyramid-receiving connector.
Figure 15D:
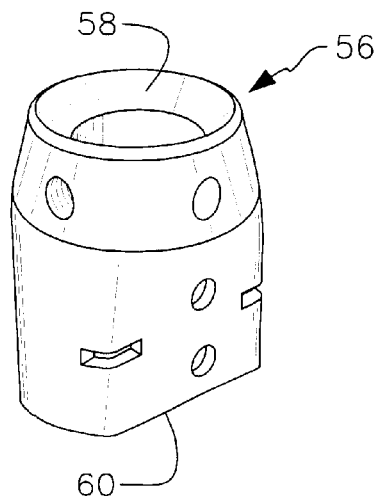
FIG. 15D is a second perspective view of said pyramid-receiving connector.

FIGS. 15A and 15B provide a more detailed perspective view of pyramid connector 50 and pyramid-receiving connector 56. FIGS. 15C and 15D provide a more detailed perspective view of pyramid-receiving connector 56.

The thickness of upper member 30a is substantially different from the thickness of upper member 30b to provide a controlled elastic response. More specifically, the different thickness shifts loads from the lateral section to the medial section. This performs the function of eliminating the flat spot of earlier prosthetic feet because such construction provides a smooth transition from heel strike to push off. Moreover, the bifurcated construction of pylon supports 32, 34 (FIGS. 1–6) or pylons 32a, 34a (FIGS. 7–12) and the greater thickness of lateral pylon support 32 or pylon 32a and upper member 30a enhance the stability of the user because said greater thickness serves to shift the weight of the user toward the medial side of the foot and thus harnesses the stabilizing power of the sound foot that opposes the prosthetic foot.

The novel structure further enhances the medial lateral stability, the torsional flex, and the anisotropic stiffness of foot 10.

Moreover, two pylons are superior to a single pylon from the standpoint of torsional characteristics. Some torsion in the shin, and more precisely torsion that can be controlled by the thickness and geometry of the cross section, is advantageous over totally rigid pylons. For example, golf and other activities require torsion in the shin.

It is also very significant that the novel prosthetic foot can flex in the medial lateral plane without having relative moving parts that bear against one another.

It will thus be seen that the objects set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

Now that the invention has been described,
What is claimed is:

1. A dynamic prosthetic foot having multiple load points and a pair of upper sections, comprising:
   a sole having a heel end and a toe end that are in substantially coplanar relation with one another;
   an upper member that overlies said sole, said upper member having a heel end and a toe end;
   said upper member having a pair of flat, transversely spaced apart, pylon supports formed in its heel end;
   said heel end of said upper member having a gradual ninety degree bend formed therein so that said pylon supports are disposed substantially perpendicular to said sole, said heel end of said upper member separating from said sole along a parting line that is transverse to a longitudinal axis of said prosthetic foot;
   said pylon supports including a lateral, anterior pylon support and a medial, posterior pylon support;
   an elongate slot formed in said heel end of said upper member, said slot substantially coincident with the longitudinal axis of said prosthetic foot and said slot extending from an uppermost end of said heel end of said upper member to a preselected point that is about two-thirds the distance from said heel end to said toe end;
   said elongate slot dividing said upper member into a pair of upper sections that respond substantially independently to forces acting upon said upper member;
   whereby forces acting on said lateral, anterior pylon support are substantially confined to said lateral, anterior pylon support and forces acting on said medial, posterior pylon support are substantially confined to said medial, posterior pylon support;
   whereby forces appearing on said lateral, anterior pylon support are similar to forces appearing on a fibula of a natural leg;
   whereby forces appearing on said medial, posterior pylon support are similar to forces appearing on a tibia of a natural leg;
   whereby forces acting upon a lateral section of said upper member are substantially attenuated when transmitted to the medial section of said upper sections; and
   whereby forces acting upon a medial section of said upper member are substantially attenuated when transmitted to the lateral section of said upper member.

2. The dynamic prosthetic foot of claim 1, wherein said lateral pylon support has a greater thickness than said medial pylon support, said greater thickness imparting greater stiffness so that forces applied to said lateral pylon support and said medial pylon support are transferred more to said medial pylon support than to said lateral pylon support, thereby mimicking the reaction of a natural foot to forces applied thereto.

3. The dynamic prosthetic foot of claim 1, wherein said upper lateral member has greater thickness than said upper medial member, said greater thickness imparting greater stiffness so that forces applied to said lateral upper member encounter less elastic response than forces applied to said medial upper member thereby mimicking the reaction of a natural foot to forces applied thereto.

4. The dynamic prosthetic foot of claim 1, wherein said sole has a first convexity formed in said heel end that performs the function of the bottom of a natural heel.

5. The dynamic prosthetic foot of claim 4, wherein said sole has a concavity longitudinally spaced from said first convexity, said concavity performing the function of a natural arch.

6. The dynamic prosthetic foot of claim 5, wherein said sole has a second convexity longitudinally spaced from said concavity, said second convexity performing the function of the ball of a natural foot.

7. The dynamic prosthetic foot of claim 6, wherein said preselected point is an inflection point where a downward slope of said concavity meets an upward slope of said second convexity.

8. The dynamic prosthetic foot of claim 1, further comprising a pylon connector secured to each of said pylon supports on a trailing side thereof.

9. The dynamic prosthetic foot of claim 1, wherein said sole and a part of said upper member disposed between said parting line and said toe end of said sole are formed integrally with one another.

10. A dynamic prosthetic foot having multiple load points and an anterior/posterior upper section, comprising:
    a sole having a heel end and a toe end in substantially coplanar relation with one another;
    an upper member that overlies said sole, said upper member having a heel end and a toe end;
    said upper member having a pair of flat, transversely spaced apart pylons formed in its heel end;
    said heel end of said upper member having a gradual ninety degree bend formed therein so that said pylons are disposed substantially perpendicular to said sole, said heel end of said upper member separating from said sole along a parting line that is transverse to a longitudinal axis of said prosthetic foot;

said pylons including a lateral, anterior pylon and a medial, posterior pylon;

an elongate slot formed in said heel end of said upper member, said slot substantially coincident with a longitudinal axis of said prosthetic foot and said slot extending from an uppermost end of said heel end of said upper member to a preselected point that is about two-thirds the distance from said heel end to said toe end;

said elongate slot dividing said upper member into a pair of upper sections that respond substantially independently to forces acting upon said upper member;

whereby forces acting on said lateral, anterior pylon are substantially confined to said lateral, anterior pylon and forces acting on said medial, posterior pylon are substantially confined to said medial, posterior pylon;

whereby forces appearing on said lateral, anterior pylon are similar to forces appearing on a fibula of a natural leg;

whereby forces appearing on said medial, posterior pylon are similar to forces appearing on a tibia of a natural leg.

11. The dynamic prosthetic foot of claim 10, further comprising:

said lateral pylon having a greater thickness than said medial pylon;

said greater thickness imparting greater stiffness so that forces applied to said lateral pylon and said medial pylon are applied more to said medial pylon than to said lateral pylon, thereby mimicking the reaction of a natural foot to forces applied thereto.

12. The dynamic prosthetic foot of claim 10, wherein said lateral section of said lateral upper member has a greater thickness than said medial section of said medial upper member, said greater thickness imparting greater strength so that forces applied to said lateral upper member are provided with less of an elastic response than forces applied to said medial upper member, thereby mimicking the reaction of a natural foot to forces applied thereto.

13. The dynamic prosthetic foot of claim 10, wherein said sole has a first convexity formed in said heel end that performs the function of the bottom of a natural heel.

14. The dynamic prosthetic foot of claim 12, wherein said sole has a concavity longitudinally spaced from said first convexity, said concavity performing the function of a natural arch.

15. The dynamic prosthetic foot of claim 13, wherein said sole has a second convexity longitudinally spaced from said concavity, said second convexity performing the function of the ball of a natural foot.

16. The dynamic prosthetic foot of claim 14, wherein said preselected point is an inflection point where a downward slope of said concavity meets an upward slope of said second convexity.

17. The dynamic prosthetic foot of claim 10, wherein said sole and a part of said upper member disposed between said parting line and said toe end of said sole are formed integrally with one another.

18. The dynamic prosthetic foot of claim 10, wherein said lateral and medial pylons are laminated at respective uppermost ends thereof to a prosthetic socket.

19. The dynamic prosthetic foot of claim 10, wherein said lateral and medial pylons are connected at respective uppermost ends thereof to a connector member and wherein said connector member is laminated to a prosthetic socket.

20. The dynamic prosthetic foot of claim 10, wherein said lateral and medial pylons are connected at respective uppermost ends thereof to a pyramid-receiving connector that engages a pyramid that depends from said prosthetic socket.

* * * * *